(12) United States Patent
Bonrath et al.

(10) Patent No.: US 6,700,002 B2
(45) Date of Patent: Mar. 2, 2004

(54) PROCESS FOR MAKING VITAMIN E USING HYDROGEN-TRIS(OXALATO) PHOSPHATE

(75) Inventors: Werner Bonrath, Freiburg (DE); Thomas Netscher, Bad Krozingen (DE); Ulrich Wietelmann, Friedrichsdorf (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 10/053,297

(22) Filed: Jan. 17, 2002

(65) Prior Publication Data

US 2002/0161247 A1 Oct. 31, 2002

(30) Foreign Application Priority Data

Jan. 18, 2001 (EP) .............................. 01101026

(51) Int. Cl.$^7$ ............................................ C07D 311/08
(52) U.S. Cl. ...................................................... 549/411
(58) Field of Search ............................ 549/411; 558/73

(56) References Cited

U.S. PATENT DOCUMENTS 2,230,659 A     2/1941     von Werder
5,886,196 A     3/1999     Fürbringer

FOREIGN PATENT DOCUMENTS

GB     811895     *     4/1959

OTHER PUBLICATIONS

CA 124:248655.*

Lamande, et al., "Structure Et Acidite De Composes A Atome De Bore Et De Phosphore Hypercoordonnes," *Journal of Organometallic Chemistry*, vol. 329, pp. 1–29 (1987).

* cited by examiner

*Primary Examiner*—Joseph K. McKane
*Assistant Examiner*—Ebenezer Sackey
(74) *Attorney, Agent, or Firm*—Bryan Cave LLP

(57) ABSTRACT

A process for the manufacture of (all-rac)-α-tocopherol by the catalyzed reaction of trimethylhydroquinone with isophytol or phytol is characterized by carrying out the reaction in the presence of hydrogen tris(oxalato)phosphate, or an adduct thereof with a solvent, as the catalyst in an organic solvent. The product of the process is the most active and industrially most important member of the vitamin E group.

22 Claims, No Drawings

PROCESS FOR MAKING VITAMIN E USING HYDROGEN-TRIS(OXALATO) PHOSPHATE

FIELD OF THE INVENTION

The present invention is concerned with a novel process for the manufacture of (all-rac)-α-tocopherol by the acid-catalyzed reaction of trimethylhydroquinone (TMHQ) with isophytol (IP) or phytol (PH) in a solvent.

BACKGROUND OF THE INVENTION

As is known, (all-rac)-α-tocopherol (or as it has mostly been denoted in the prior art, "d,l-α-tocopherol") is a diastereoisomeric mixture of 2,5,7,8-tetramethyl-2-(4',8',12'-trimethyl-tridecyl)-6-chromanol (α-tocopherol), which is the most active and industrially most important member of the vitamin E group.

Many processes for the manufacture of "d,l-α-tocopherol" by the reaction of TMHQ with IP or PH in the presence of a catalyst or catalyst system and in a solvent or solvent system are described in the literature. These processes go back to the work of Karrer et al., Bergel et al. as well as Smith et al. (see Helv. Chim. Acta 21, 520 et seq. (1938), Nature 142, 36 et seq. (1938) and, respectively, Science 88, 37 et seq. (1938) and J. Am. Chem. Soc. 61, 2615 et seq. (1939)). While Karrer et al. carried out the synthesis of d,l-α-tocopherol from TMHQ and phytyl bromide in the presence of anhydrous zinc chloride ($ZnCl_2$; a Lewis acid), not only Bergel et al. but also Smith et al. used TMHQ and PH as starting materials. In the following years alternative solvents and Lewis acids were developed. From the work of Karrer et al. there was developed in the year 1941 a technically interesting process for the manufacture of d,l-α-tocopherol which was based on the reaction of TMHQ with IP in the presence of the catalyst system $ZnCl_2$/hydrochloric acid (HCl) (U.S. Pat. No. 2,411,969, which is hereby incorporated by reference as if recited in full herein). Later publications, e.g. Japanese Patent Publications (Kokai) 54380/1985, 64977/1985 and 226979/1987 (Chemical Abstracts (C.A.) 103, 123731s (1985), C.A. 103, 104799d (1985) and, respectively, C.A. 110, 39217r (1989)), describe this reaction in the presence of zinc and/or $ZnCl_2$ and a Bronsted (protonic) acid, such as a hydrohalic acid, e.g. HCl, trichloroacetic acid, acetic acid and the like, especially $ZnCl_2$/HCl, as the catalyst system. Disadvantages of these and further published processes featuring $ZnCl_2$ in combination with a Bronsted acid are the corrosive properties of the acids and the contamination of the waste water with zinc ions as a result of the large amount of $ZnCl_2$ required for the catalysis.

The manufacture of d,l-α(-tocopherol by the reaction of TMHQ with phytyl chloride, PH or IP in the presence of boron trifluoride ($BF_3$) or its etherate ($BF_3Et_2O$) is described in German Patents 960720 and 1015446 as well as in U.S. Pat. No. 3,444,213, which is hereby incorporated by reference as if recited in full herein. However $BF_3$ too has corrosive properties.

Also, the reaction of TMHQ with IP or PH in the presence of a Lewis acid, e.g. $ZnCl_2$, $BF_3$ or aluminum trichloride ($AlCl_3$), a strong acid, e.g. HCl, and an amine salt as the catalyst system is described in European Patent Publication (EP) 100471. In an earlier patent publication, DOS 2606830, the IP or PH is pretreated with ammonia or an amine before the reaction with TMHQ in the presence of $ZnCl_2$ and an acid is effected. In both cases corrosion problems occur.

A further interesting method for the manufacture of d,l-α-tocopherol from TMHQ and IP includes using an isolated TMHQ-$BF_3$ or —$AlCl_3$ complex and a solvent mixture featuring a nitro compound (DOS 1909164). This process avoids to a large extent the formation of undesired by-products because it involves mild reaction conditions. The yield of d,l-α-tocopherol, based on IP and the use of the solvent mixture methylene chloride/nitromethane, is reported as 77%. However, the use of such a solvent mixture is disadvantageous because nitro compounds tend to be unstable when excessively heated, so that difficulty is encountered in the product isolation, solvent separation and recycling procedures.

The manufacture of d,l-α-tocopherol by the reaction of TMHQ with IP using cation exchange resin complexes of metal ions ($Zn^{2+}$, $Sn^{2+}$ and $Sn^{4+}$) is disclosed in Bull. Chem. Soc. Japan 50, 2477–2478 (1977); amongst other disadvantages the reaction produces the product in unsatisfactory yields.

The use of macroreticular ion exchangers, e.g. Amberlyst® 15, as the catalyst for the reaction of TMHQ with IP is described in U.S. Pat. No. 3,459,773, which is hereby incorporated by reference as if recited in full herein. However, the d,l-α-tocopherol could not be obtained in the requisite purity.

EP 603695 discloses the manufacture of d,l-α-tocopherol in liquid or supercritical carbon dioxide by the reaction of TMHQ with IP or PH in the presence of acidic catalysts, such as $ZnCl_2$/HCl and ion exchangers. The reported yields are unsatisfactory.

The reaction in the presence of a catalyst system which consists of iron(II) chloride, metallic iron and HCl gas or aqueous solution is described in DOS 2160103 and U.S. Pat. No. 3,789,086, which is hereby incorporated by reference as if recited in full herein. The formation of less by-products is advantageous compared with the aforementioned process using $ZnCl_2$/HCl. However, corrosion problems and chloride contamination are equally disadvantageous.

An alternative for the reaction of TMHQ with IP to form d,l-α-tocopherol includes using trifluoroacetic acid or its anhydride as the catalyst (EP 12824). Although in this process the avoidance of HCl is achieved, the catalyst is also corrosive, and relatively expensive.

The use of a heteropoly acid such as 12-tungstophosphoric or 12-tungstosilicic acid as the catalyst for the reaction of TMHQ with IP was described in React. Kinet. Catal. Lett. 47(1), 59–64 (1992). d,l-α-Tocopherol could be obtained, using various solvents, in about 90% yield.

A further process described in the literature (EP 658552; Bull. Chem. Soc. Japan 68, 3569–3571 (1995)) for the synthesis of d,l-α-tocopherol is based on the use of a various lanthanide trifluoromethanesulphonates (triflates), e.g. scandium trifluoromethane-sulphonate, as the catalyst for the reaction. With up to about 10% excess of IP this process gives yields up to 98%.

The use of ion-exchanged bentonite, montmorillonite or saponite through treatment with e.g. scandium chloride and other metal salts (yttrium, lanthanum, etc.) as the catalyst for the reaction of TMHQ with IP or PH has as a disadvantage the need for a large amount of catalyst (EP 677520; Bull. Chem. Soc. Japan 69, 137–139 (1996)).

According to the Examples of EP 694541, the reaction of TMHQ with IP to α-tocopherol can be achieved in high yields and with a high product purity when such solvents as carbonate esters, fatty acid esters and certain mixed solvent systems are employed, the exemplified catalysis being effected by $ZnCl_2$/HCl. Disadvantages in this process are, in addition to the contamination of the waste water by zinc ions, the usual large "catalyst amount" of $ZnCl_2$ used.

According to WO 97/28151, the acid-catalyzed reaction of TMHQ with IP can be performed in a cyclic carbonate or α-lactone as the solvent. The preferred catalyst is a mixture of orthoboric acid and oxalic, tartaric or citric acid, or boron trifluoride etherate.

In EP 784042, there is disclosed the use of hydrogen bis(oxalato)borate as a protonic acid catalyst in various condensation reactions, e.g. Friedel-Crafts condensations, including the acid-catalyzed reaction of TMHQ with IP to produce d,l-α-tocopherol.

WO 98/21197 discloses the manufacture of d,l-α-tocopherol from TMHQ and IP using bis (trifluoromethylsulphonyl)imide or a metal salt thereof optionally together with a strong Bronsted acid, as catalyst in such types of aprotic solvents as aliphatic and cyclic ketones or esters, and aromatic hydrocarbons.

Using the same kind of bis(trifluoromethylsulphonyl) imide catalyst it has been shown in EP 1000940 that the dl-α-tocopherol manufacturing process can also be realized in supercritical carbon dioxide or nitrous oxide as the solvent.

From the foregoing review it is evident that the previously known processes have considerable disadvantages. For example, corrosion problems occur in all processes in which such acid catalysts as boron trifluoride are used. Toxicity problems with the boron trifluoride adducts also occur, and when iron or zinc is used there is a contamination of the waste water with the metal ions which is today no longer acceptable. In some of these processes, the formation of undesired by-products, e.g. phytyltoluene and chlorophytols, is an especially serious problem. And, in most cases the yields are unsatisfactory.

SUMMARY OF THE INVENTION

An object of the present invention is to provide a process for the manufacture of (all-rac)-α-tocopherol by the reaction of trimethylhydroquinone with isophytol or phytol in the presence of a catalyst and in a solvent which does not have the disadvantages of previously known procedures. In this respect, it is necessary that the catalyst used has no, or at least a much reduced, corrosive action, is non-toxic, does not contaminate the environment, e.g. with chlorinated by-products or heavy metal ions, and catalyzes the desired reaction as selectively as possible and in high yields.

Furthermore, the catalyst should display its activity in small, really catalytic, amounts and should be readily separable and re-usable several times.

One embodiment of the invention is a process for making (all-rac)-α-tocopherol comprising contacting a reaction mixture comprising trimethylhydroquinone and isophytol or phytol with a catalyst comprising hydrogen tris(oxalato) phosphate and an organic solvent or the reaction mixture.

The hydrogen tris(oxalato)phosphate used as the catalyst in the process in accordance with the present invention is a compound of the formula:

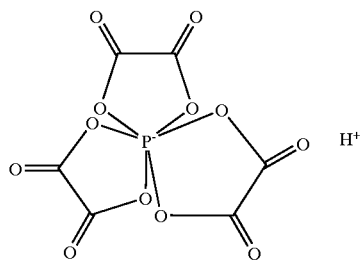

Said hydrogen tris(oxalato)phosphate may be produced by contacting phosphorus pentachloride with oxalic acid and an aprotic organic solvent.

The object of the present invention is achieved by carrying out the reaction of trimethylhydroquinone with isophytol or phytol in the presence of hydrogen tris-(oxalato) phosphate as the catalyst in an organic solvent.

DETAILED DESCRIPTION OF THE INVENTION

In the present invention, the reaction to form (all-rac)-α-tocopherol is represented in the following Reaction Scheme, showing the reaction with IP only:

Reaction Scheme

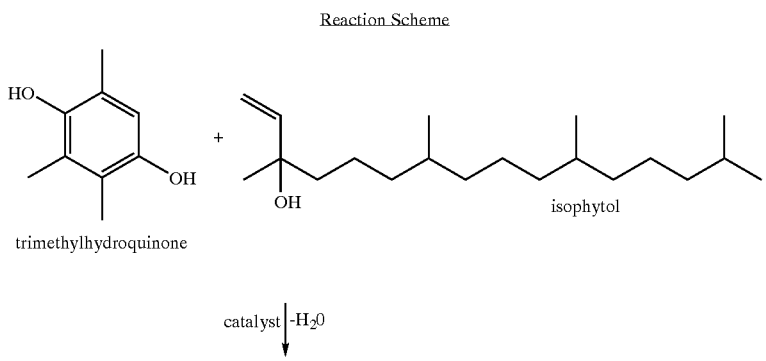

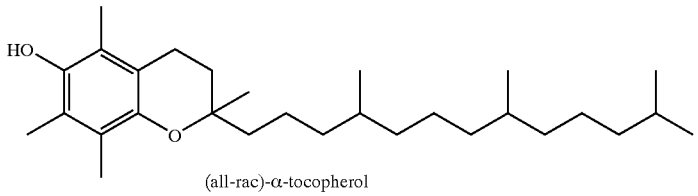

(all-rac)-α-tocopherol

Accordingly, the process in accordance with the present invention for the manufacture of (all-rac)-α-tocopherol by the catalyzed reaction of trimethylhydroquinone with isophytol or phytol is characterized by carrying out the reaction in the presence of hydrogen tris(oxalato)phosphate as the catalyst in an organic solvent.

The catalyst, which has the following formula

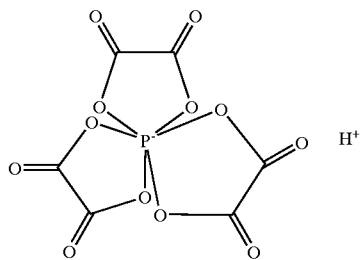

has not been previously disclosed. This new catalyst may be produced very simply by reacting phosphorus pentachloride with oxalic acid in an aprotic organic solvent, whereby the hydrogen chloride gas generated in the reaction is removed from the reaction mixture. This reaction is represented by the equation:

$$PCl_5 + 3(COOH)_2 \rightarrow [P^-(C_2O_4)_3]H^+ + 5HCl$$

The oxalic acid should be as anhydrous as possible, such as can be achieved by pre-drying treatment with a desiccating agent, e.g. according to well-known procedures. The reaction for producing hydrogen tris(oxalato)phosphate can be effected in practice either by adding the phosphorus pentachloride to the oxalic acid in the solvent or by adding the oxalic acid to the phosphorus pentachloride in the solvent, the addition in each case being portionwise. As the aprotic organic solvent there is suitably used a lower aliphatic mono- or diether, e.g. diethyl ether or, respectively, dimethoxyethane; a cyclic ether, e.g. tetrahydrofuran; a lower dialkyl carbonate, e.g. dimethyl or diethyl carbonate; an alkylene carbonate, e.g. ethylene or propylene carbonate; a $C_{5-12}$-alkane; an aromatic hydrocarbon, e.g. benzene or toluene; a partially or per-halogenated aliphatic or aromatic hydrocarbon; or a mixture of two or more of the aforementioned aprotic organic solvents. Depending on the solvation potential of the employed solvent both the reactants will be at least partially dissolved therein or present in suspension therein, e.g. in the latter case when a hydrocarbon is used as the solvent. The reaction to produce the hydrogen tris (oxalato) phosphate is carried out in a temperature range from about −20° C. to about +120° C., preferably at temperatures from about 0° C. to about 100° C. The molar ratio of the oxalic acid to the phosphorus pentachloride is suitably 3.1 (equivalent proportions) or slightly higher, i.e. where the oxalic acid is in slight excess. As used herein, "slightly higher" or "in slight excess" means that no more than about 5% excess of oxalic acid is employed. During the reaction hydrogen chloride gas is continuously generated, and its efficient separation from the reaction mixture can be promoted in various ways, e.g. by "stripping" using a continuous passage of an inert gas, e.g. nitrogen or argon, through the mixture, by effecting the reaction under reduced pressure or with continuous distillative removal of solvent from the mixture, by heating the mixture on termination of the reaction under reflux, or by a combination of two or more of such process measures. In certain cases, e.g. when using diethyl ether as the solvent, the generated hydrogen chloride can also be removed by liquid/liquid separation: in such a case the reaction mixture forms into two liquid phases, i.e. a lower, denser phase containing the desired hydrogen tris(oxalato)phosphate in the form of its ether complex with very little, i.e., less than 5 wt. % of, hydrogen chloride, and an upper, less dense phase in which the hydrogen chloride accumulates and in which, due to the poor solubility of the product in ether, hardly any product is present. The upper phase can be removed from the lower phase, and the latter extracted one or more times with ether to remove any hydrogen chloride present. The remaining oily phase, consisting largely of the hydrogen tris(oxalato)phosphate diethyl etherate adduct (particularly of the formula [P⁻(C₂O₄)₃]H⁺·4(C₂H₅)₂O), can then be subjected to reduced pressure drying at room temperature for several minutes to remove unbound ether solvent and at least some of the bound ether, if desired, whereby the oil transforms to a crystalline solid. The exact composition of the adduct depends on the conditions of drying in each case. A typical adduct with diethyl ether features on average about 2 molecules of diethyl ether per molecule of hydrogen tris (oxalato)phosphate.

Depending on various factors, such as the batch weights, the rate of reactant addition, the employed solvent and the reaction temperature, the actual reaction to produce hydrogen tris(oxalato)phosphate is normally complete within several minutes to a few hours.

The catalyst can be used in the process for making (all-rac)-α-tocopherol without purification, and for example can be used despite containing some solvent remaining from its preparation, particularly because it may even be added in solution, for example in an aliphatic ether or a dialkyl or alkylene carbonate, for example the solvent in which the catalyst was prepared. Moreover, it may be used as its adduct with a solvent, particularly an aliphatic ether, such as diethyl ether, e.g. as the solid adduct of the aforementioned formula [P⁻(C₂O₄)₃]H⁺·4(C₂H₅)₂O or further adducts with diethyl ether, e.g., and preferably, the one featuring on average about 2 molecules of diethyl ether per molecule of hydrogen tris(oxalato)phosphate. Such adducts with diethyl ether are preferred forms of the catalyst for use in the process of the present invention.

In respect of the process for manufacturing (all-rac)-α-tocopherol in accordance with the present invention it has been surprisingly found that as a result of the use of the catalyst hydrogen tris(oxalato)phosphate, which is a Bronsted acid, only small amounts of the undesirable by-products phytadienes are formed, although it is known from the chemical literature that alcohols, in particular allylic alcohols (e.g. IP or PH), easily dehydrate in the presence of acids. Other advantages of the new catalyst are its easy and cheap preparation, and the absence of heavy metals and sulfur- and fluorine-containing compounds in the process.

Solvents which can be used with the present process include polar aprotic and non-polar organic solvents. Suitable classes of polar aprotic organic solvents include aliphatic and cyclic ketones, e.g. diethyl ketone and isobutyl methyl ketone and, respectively, cyclopentanone and isophorone; cyclic esters, e.g. γ-butyrolactone; and dialkyl and alkylene carbonates, e.g. dimethyl carbonate and diethyl carbonate, and respectively, ethylene carbonate and propylene carbonate. Examples of classes of non-polar organic solvents that may be used in the process include aliphatic hydrocarbons, e.g. hexane, heptane and octane, and aromatic hydrocarbons, e.g. benzene, toluene and the xylenes. Mixtures of two or more of each type of solvent also can be used. The reaction can be effected in a single solvent phase, especially in a polar aprotic organic solvent, e.g. in γ-butyrolactone or propylene carbonate, alone as the solvent, or in a biphasic solvent system, especially one consisting of a polar aprotic organic solvent, e.g. ethylene and/or propylene carbonate, as the one phase and a non-polar organic solvent, e.g. heptane, as the other phase.

The process is conveniently carried out at temperatures from about 50° C. to about 150° C., preferably from about 90° C. to about 125° C., and most preferably from about 105° C. to about 120° C.

Furthermore, the molar ratio of trimethylhydroquinone to isophytol/phytol present in the reaction mixture conveniently extends from about 1:1 to about 2.5:1, preferably from about 1.5:1 to about 2.2:1, and is most preferably about 2:1.

The amount of catalyst used is such that the molar ratio of catalyst to the educt (trimethylhydroquinone or isophytol/phytol) which is in the lesser molar amount (usually the isophytol or phytol rather than the trimethylhydroquinone) is conveniently about 0.005:100 to about 4:100, i.e. the amount of catalyst is conveniently from about 0.005 mole % to about 4 mole % of the amount of educt present in the reaction mixture in the lesser molar amount. As used herein, the expression "amount of catalyst" means the weight of pure hydrogen tris(oxalato)phosphate, i.e. of the formula $[P^-(C_2O_4)_3]H^+$, present, even though the catalyst may be impure and/or in the form of an adduct with a solvent, e.g. diethyl ether.

Conveniently about 10-100 ml, preferably about 20–40 ml, of organic solvent are used per 10 mmol of isophytol or phytol, whichever is employed.

If the process is carried out in a biphasic solvent system, especially one consisting of a polar aprotic organic solvent, e.g. an alkylene carbonate such as ethylene or propylene carbonate, and a non-polar organic solvent, e.g. an aliphatic hydrocarbon such as heptane, then the volume ratio of the non-polar solvent to the polar solvent is conveniently in the range from about 0.3:1 to about 5:1, preferably from about 1:1 to about 3:2.

Moreover, the process is conveniently carried out under an inert gas atmosphere, preferably gaseous nitrogen or argon.

The actual reaction generally lasts for about 0.2 to about 20 hours, preferably about 0.5 to about 1 hour.

The process in accordance with the invention can be carried out batchwise or continuously, preferably continuously, and in general operationally in a very simple manner, for example by adding isophytol or phytol, as such, i.e. alone, in undiluted form, or in solution, portionwise to a suspension or solution of the trimethylhydroquinone and the catalyst. The rate at which the isophytol or phytol is added is not critical. Conveniently, isophytol/phytol is added continuously over a period of about 3 minutes to about 3 hours, preferably about 5 minutes to about 1.5 hours. After completion of the isophytol/phytol addition and the appropriate subsequent reaction period, generally about 0.2 to about 20 hours, the working-up is effected by procedures conventionally used in organic chemistry.

If desired, the obtained (all-rac)-α-tocopherol can be converted into its acetate, succinate, poly(oxyethylene) succinate, nicotinate and further known application forms by standard procedures.

The process for forming (all-rac)-α-tocopherol in accordance with the invention enables the catalyst used to be separated readily and to be reused several times.

Advantages in the use of the catalyst in the process in accordance with the invention are, in addition to high yields of (all-rac)-α-tocopherol, the avoidance of corrosion, the avoidance of waste water contamination with heavy metal ions, the high selectivity as well as the enabled ready isolation of the produced (all-rac)-α-tocopherol from the mixture after reaction. Furthermore, the amount of dehydration products, so-called phytadienes, which tend to result from the action of acids on allylic alcohols such as isophytol and phytol, is kept to an acceptable minimum in the process of the present invention, as is also the amount of furan derivatives which tend to be produced as by-products in dl-α-tocopherol manufacture (see, for example, Bull. Chem. Soc. Japan 68, 3569–3571 (1995)).

The following examples are provided to further illustrate the process of the present invention. These examples are illustrative only and are not intended to limit the scope of the invention in any way.

EXAMPLES

Example 1

Preparation of Hydrogen tris(oxalato)phosphate (Catalyst)
Procedure (a):

In a 500 ml three-necked reaction flask 52.95 g (588 mmol: 3% excess quantity) of oxalic acid were dissolved in 300 ml of diethyl ether. The solution of oxalic acid was treated slowly and continuously within 5 minutes with 39.59 g (190.2 mmol) of phosphorus pentachloride from a powder funnel, during the addition of which the reaction mixture warmed up to the reflux temperature. After completion of the phosphorus pentachloride addition the reaction mixture was held at reflux temperature for 2 hours, during which altogether 6.5 l (approx. 270 mmol, being approx. 28% of the theoretical amount) of hydrogen chloride gas had been generated and removed.

The mixture was then allowed to cool to room temperature. From the resulting two-phase fluid the upper phase was separated off and the lower phase washed four times with 200 ml of diethyl ether in each case. An analysis of the initially removed upper phase and the four washings (upper phases) indicated that the acid content, initially 3.90 mmol/g (total 720 mmol), became rapidly less with each washing (finally, in the fourth washing, 0.061 mmol/g, total 8 mmol).

The remaining lower phase was evaporated to dryness under reduced pressure, at a final bath temperature of 70° C., affording a finely crystalline white solid, being the desired hydrogen tris(oxalato)phosphate in the form of an adduct with diethyl ether.

Procedure (b):

In a 1 l four-necked reaction flask fitted with an intensive condenser, a thermoelement, a KPG stirrer and a heating mantle 158.9 g (1.764 mol) of dried oxalic acid dissolved in 490 g (700 ml) of diethyl ether were treated slowly and continuously within 20 minutes with 118.8 g (0.572 mol) of phosphorus pentachloride from a powder funnel. During the addition the reaction mixture warmed up to the reflux temperature (36° C.) with relatively strong generation of gas (hydrogen chloride). After completion of the phosphorus pentachloride addition the reaction mixture was held at reflux temperature for 140 minutes, during which altogether 17.01 (approx. 0.688 mol, being approx. 14% of the theoretical amount) of hydrogen chloride gas had been generated.

The mixture was then allowed to cool to room temperature. From the resulting two-phase fluid the upper phase was separated off and the lower phase, containing the desired product, was washed five times with about 120 g of diethyl ether in each case. As in the previous procedure the analysis of the initially removed upper phase and the washings indicated that the acid content became rapidly less from the initially removed upper phase to the last washing phase.

The remaining lower phase, an oil, was analyzed by $C_6D_6$ spectroscopy, from which it was established that it consisted principally of a diethyl ether adduct of hydrogen tris(oxalato)-phosphate featuring about four $(C_2H_5)_2O$ units per molecule. About 20 ml of the oily hydrogen tris(oxalato) phosphate-diethyl ether adduct was dried under reduced pressure at room temperature for 10 minutes. Within a short time the oil was observed to solidify, the resulting solid weighing 17.7 g. Drying was continued for a further 3 hours at room temperature and 2 hours at 45-50° C., after which the weight remained constant at 14.1 g. The weight loss corresponded with the removal of one mole of diethyl ether per mole of hydrogen tris(oxalato)phosphate. The product consisted of finely crystalline hydrogen tris(oxalato) phosphate in the form of its adduct with diethyl ether, of which the analysis indicated a phosphorus (P) content of 2.7 mmol per gram.

Example 2

7.56 g (49.5 mmol) of trimethylhydroquinone were suspended in the employed solvent or solvent mixture, whereby in the case of a single solvent, i.e. γ-butyrolactone, diethyl ketone or propylene carbonate, 50 ml of such solvent were used, and the case of a solvent mixture of an alkylene carbonate, i.e. ethylene and/or propylene carbonate, and an aliphatic hydrocarbon, i.e. heptane, 50 ml of each were used. Thereafter, about 0.5 or about 1.0 mole % (based on the amount of isophytol used) of the catalyst hydrogen tris (oxalato)phosphate in the form of its adduct with an estimated 3.3 molecules of diethyl ether per molecule was added. Then the mixture was heated to a temperature in the range of 5–150° C., and 10 g (11.9 ml; 33 mmol) of isophytol were added portionwise to the mixture over a period of about 20 minutes under an argon atmosphere. Subsequently, the reaction mixture was stirred under argon for a further 30 minutes at reflux temperature and monitored by thin layer chromatography to follow the progress of the reaction. After the establishment of completed conversion to (all-rac)-α-tocopherol this product was recovered from the reaction mixture by cooling it to about 60–80° C., separating the phases (if appropriate) and distilling off the solvent under reduced pressure.

Unambiguous identification of the product was effected by comparison of gas chromatographic retention times with those of an authentic sample.

The results are presented in the following Table 1.

TABLE 1

Results of the use of the catalyst hydrogen tris(oxalato)phosphate in the manufacture of (all-rac)-α-tocopherol using various solvents

| Amount of catalyst (mg) | Solvent (ml) | Yield (%) |
| --- | --- | --- |
| 50 | Ethylene carbonate/heptane (50/50) | 92.4 |
| 53 | Propylene carbonate/heptane (50/50) | 86.2 |
| 52.5 | Jeffsol ®/heptane (50/50) | 88.9 |
| 48.5 | γ-Butyrolactone (50) | 80.7 |
| 55.5 | Diethyl ketone (50) | 60.0 |
| 104 | Propylene carbonate (50) | 74.7 |

Jeffsol® is a 1:1 mixture of ethylene carbonate and propylene carbonate, commercially available from Huntsman Corp., P.O. Box 15730, Austin, Tex. 78761, USA/Antwerp 2030, Belgium.

Example 3

The procedure of Example 2 was repeated with the differences that various mole % amounts of catalyst were used (based on the amount of isophytol used), and the solvent was in all cases the biphasic solvent system 50 ml of Jeffsol® and 50 ml of heptane. The results are presented in the following Table 2.

TABLE 2

Results of the use of the catalyst hydrogen tris(oxalato)phosphate in the manufacture of (all-rac)-α-tocopherol using various amounts of catalyst

| Amount of catalyst (mg) | Yield (%) |
| --- | --- |
| 20 | 90.6 |
| 50.5 | 88.5 |
| 52.5 | 88.9 |
| 55 | 88.7 |
| 108.8 | 85.9 |

Example 4

The procedure of Example 2 was repeated using various mole % amounts of catalyst, various biphasic solvent systems, and varying the time of addition of the isophytol (IP). The results are presented in the following Table 3.

TABLE 3

Influence of IP addition time

| Amount of catalyst (mg) | Solvent (all 50 ml/50 ml biphasic systems) | IP addition time (min.) | Yield (%) |
| --- | --- | --- | --- |
| 42.1 | Ethylene carbonate/heptane | 20 | 89.0 |
| 50.0 | Ethylene carbonate/heptane | 10 | 92.4 |
| 53.0 | Propylene carbonate/heptane | 20 | 86.2 |
| 50.0 | Jeffsol ®/heptane | 120 | 72.6 |
| 51.5 | Jeffsol ®/heptane | 40 | 85.3 |
| 55.0 | Jeffsol ®/heptane | 20 | 88.7 |
| 50.5 | Jeffsol ®/heptane | 10 | 88.5 |
| 47.6 | Jeffsol ®/heptane | 5 | 84.3 |

The invention being thus described, it will be obvious that the same may be varied in many ways. Such variations are

What is claimed is:

1. A process for making (all-rac)-α-tocopherol comprising contacting a reaction mixture comprising trimethylhydroquinone and isophytol or phytol with a catalyst comprising hydrogen tris(oxalato)phosphate and an organic solvent for the reaction mixture.

2. A process according to claim 1 wherein the catalyst is added to the reaction mixture as an adduct in a catalyst solvent.

3. A process according to claim 2 wherein the catalyst solvent is an aliphatic ether.

4. A process according to claim 3 wherein the aliphatic ether is diethyl ether.

5. A process according to claim 1 wherein the catalyst for the reaction mixture is added to the reaction mixture in solution.

6. A process according to claim 5 wherein the solution is selected from the group consisting of an aliphatic ether, a dialkyl carbonate, and an alkylene carbonate.

7. A process according to claim 5 wherein the solution is a solvent used during preparation of the catalyst.

8. A process according to claim 1 wherein the reaction mixture solvent is selected from the group consisting of an aliphatic or cyclic ketone, a cyclic ester, a dialkyl or alkylene carbonate, an aliphatic or aromatic hydrocarbon, and mixtures thereof.

9. A process according to claim 8, wherein the reaction mixture solvent is selected from the group consisting of diethyl ketone, isobutyl methyl ketone, cyclopentanone, isophorone, γ-butyrolactone, dimethyl carbonate, diethyl carbonate, ethylene carbonate, propylene carbonate, hexane, heptane, octane, benzene, toluene, xylene, and mixtures thereof.

10. A process according to claim 1 wherein the reaction mixture solvent is a biphasic solvent system.

11. A process according to claim 10 wherein the biphasic solvent system comprises ethylene and/or propylene carbonate as a first phase and heptane as a second phase.

12. A process according to claim 1 wherein the amount of hydrogen tris(oxalato)phosphate used in the reaction mixture is from about 0.005 mole % to about 4 mole % based on the amount of trimethylhydroquinone or isophytol/phytol, which is present in the reaction mixture in the lesser molar amount.

13. A process according to claim 1 wherein about 10–100 ml of the organic solvent are used per 10 mmol of isophytol or phytol.

14. A process according to claim 13 wherein about 20–40 ml of the organic solvent are used per 10 mmol of isophytol or phytol.

15. A process according to claim 1 wherein the reaction is carried out at temperatures from about 50° C. to about 150° C.

16. A process according to claim 15 wherein the temperature is about 90° C. to about 125° C.

17. A process according to claim 16 wherein the temperature is from about 105° C. to about 120° C.

18. A process according to claim 1 wherein the molar ratio of trimethylhydroquinone to isophytol/phytol present in the reaction mixture is from about 1:1 to about 2.5:1.

19. A process according to claim 18 wherein the molar ratio of trimethylhydroquinone to isophytol/phytol present in the reaction mixture is from about 1.5:1 to about 2.2:1.

20. A process according to claim 19 wherein the molar ratio of trimethylhydroquinone to isophytol/phytol present in the reaction mixture is about 2:1.

21. A process according to claim 1 wherein the contacting step further comprises adding the isophytol or phytol, alone or in solution, portionwise to a suspension or solution of the trimethylhydroquinone and the catalyst.

22. A process according to claim 1 wherein the process is carried out in a continuous manner.

* * * * *